(12) United States Patent
Awata et al.

(10) Patent No.: US 8,580,196 B2
(45) Date of Patent: Nov. 12, 2013

(54) AUTOMATIC ANALYZER

(75) Inventors: Yasunao Awata, Yokohama (JP);
Kazuhiro Shimada, Hitachinaka (JP);
Yoshimitsu Takagi, Hitachinaka (JP);
Toshihide Orihashi, Hitachinaka (JP);
Shigeki Matsubara, Hitachinaka (JP);
Werner Döppen, Eberfing (DE);
Dietmar Kappelhoff, Goldau (CH)

(73) Assignees: Hitachi High-Technologies Corporation, Tokyo (JP); Roche Diagnostics Operations, Inc., Indianapolis, IN (US)

( * ) Notice: Subject to any disclaimer, the term of this patent is extended or adjusted under 35 U.S.C. 154(b) by 829 days.

(21) Appl. No.: 11/840,042

(22) Filed: Aug. 16, 2007

(65) Prior Publication Data
US 2008/0056939 A1 Mar. 6, 2008

(30) Foreign Application Priority Data

Aug. 31, 2006 (JP) .................................. 2006-234836

(51) Int. Cl.
G01N 21/00 (2006.01)
G01N 31/00 (2006.01)
G01N 33/00 (2006.01)
G05B 21/00 (2006.01)

(52) U.S. Cl.
USPC ................................ 422/67; 700/266; 702/22

(58) Field of Classification Search
None
See application file for complete search history.

(56) References Cited

U.S. PATENT DOCUMENTS

| 5,730,939 A * | 3/1998 | Kurumada et al. ............. 422/67 |
| 6,080,364 A * | 6/2000 | Mimura et al. ................. 422/67 |
| 6,090,630 A * | 7/2000 | Koakutsu et al. ............... 436/50 |
| 6,579,717 B1 | 6/2003 | Matsubara et al. |
| 2005/0175506 A1* | 8/2005 | Matsubara et al. .......... 422/68.1 |
| 2008/0014118 A1* | 1/2008 | Kitagawa et al. .............. 422/64 |

FOREIGN PATENT DOCUMENTS

| EP | 0845674 | 6/1998 |
| EP | 0871034 | 10/1998 |
| JP | 2000-310643 | 11/2000 |
| JP | 2000-321283 | 11/2000 |

OTHER PUBLICATIONS

The Notification of the Second Office Action issued in Application/Patent No. 200710140356.5, Mar. 30, 2011, 13 pp., The State Intellectual Property Office of P.R. China, China.

* cited by examiner

*Primary Examiner* — Jill Warden
*Assistant Examiner* — Charles D Hammond
(74) *Attorney, Agent, or Firm* — Mattingly & Malur, PC

(57) ABSTRACT

When a problematic reagent is identified while operating an automatic analyzer, it is required to have a plurality of screens displayed, and it is difficult for inexperienced operators to identify a problematic position of a reagent. With the present invention, control information for reagents and a calibrator required for analysis with an automatic analyzer are displayed concurrently, so that all necessary information can be referred to one screen. In the automatic analyzer according to the present invention, screen switching as required in the conventional technology is not necessary, and improved operability and visibility are provided.

1 Claim, 5 Drawing Sheets

AUTOMATIC ANALYZER

BACKGROUND OF THE INVENTION

1. Field of the Invention

The present invention relates to an automatic analyzer for analyzing biological samples such as blood and urine, and more specifically to an automatic analyzer having a function for displaying information concerning reagents used in analyzing the biological samples.

2. Description of the Related Art

An expiration date is fixed for each reagent used in an automatic analyzer, and it is important to check whether a reagent placed in the automatic analyzer has passed its expiration date. JP-A-2000-310643 discloses an automatic analyzer which automatically performs the checking as described above and also displays positions at which reagents which have expired are placed.

SUMMARY OF THE INVENTION

In the automatic analyzer described in JP-A-2000-310643, it is necessary to refer to a plurality of screens for checking problems of reagents, and therefore identification of a problematic reagent requires laborious work.

An object of the present invention is to provide an automatic analyzer with a screen on which an operator can easily check the current situation of reagents visually.

The configuration of the present invention for achieving the object above is as described below.

The present invention provides an automatic analyzer comprising means for mounting a plurality of reagents thereon, and a display means for displaying, on a screen, information concerning the reagents mounted on the reagent mounting means on a screen, the information including information on the positions of the reagents mounted, and at least one of information on remaining amounts of the reagents, information on expiration dates of the reagents, information on valid time of calibration, and information on valid time of quality control.

With the display of different types of information on one screen simultaneously, even an operator who does not have much experience can easily identify a problematic reagent. Furthermore, switching a screen, as required in the conventional techniques, is not necessary, which enables the operability and visibility of an analyzer.

DETAILED DESCRIPTION OF THE PREFERRED EMBODIMENTS

An embodiment of the present invention is described below with reference to the accompanying drawings.

Figure 1:
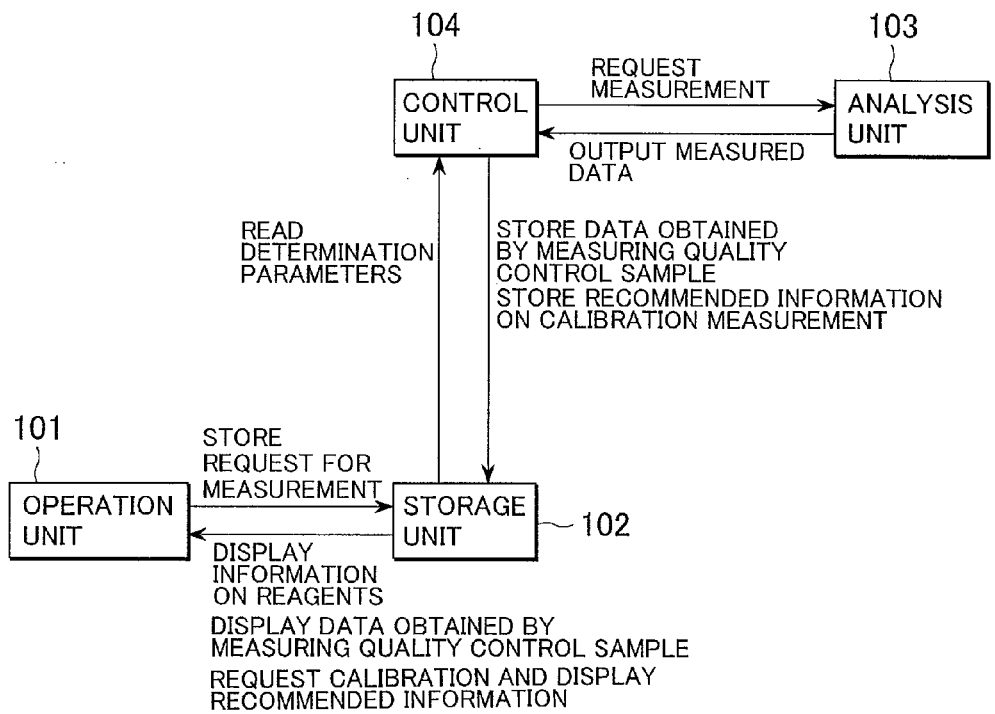
FIG. 1 is a block diagram illustrating a basic configuration of an analyzer.

FIG. 1 is a block diagram illustrating an automatic analyzer according to an embodiment of the present invention. An operating section 101 has, for instance, a keyboard and a CRT, and is used for displaying data obtained by measuring a quality control sample, a request for calibration and recommended information, or for operations for requesting measurement on a quality control sample and calibration. A storage section 102 is configured with a hard disk or the like and stores data obtained by measuring a quality control sample or recommended information on calibration measurement.

An analyzing section 103 is used for dispensing or measuring a sample.

A data processing section 104 is used, for instance, for controlling the storage section 102 or for determining measurement data.

Figure 2:
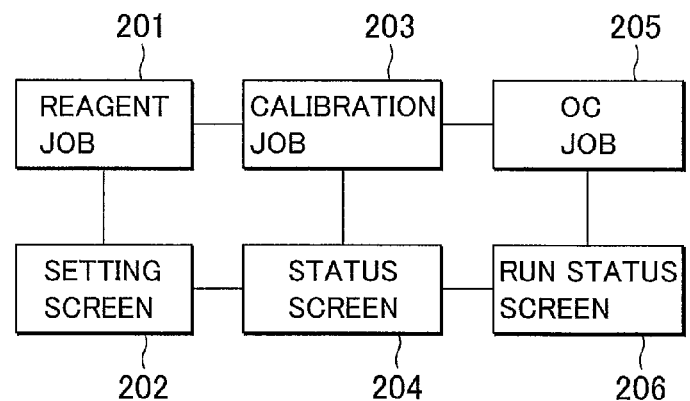
FIG. 2 is a general block diagram illustrating a screen configuration in the conventional technique.

FIG. 2 is a block diagram illustrating a screen based on the conventional technique, which is referenced when checking states of reagents, a calibrator, and quality control. To check a remaining amount of a reagent, a setting screen 202 for reagent job 201 is selected, a problematic reagent is searched in the reagent list shown on the screen. To refer to information on a reagent having any problem concerning calibration, a status screen 204 for calibration job 203 is selected for checking a problematic reagent. In the automatic analyzer based on the conventional technique, in order to refer to information on a reagent having a problem concerning quality control, a run status screen 206 for QC (quality control) job 205 is selected, and items each indicating the presence of a problem are searched in a chart shown on the screen.

Figure 3:
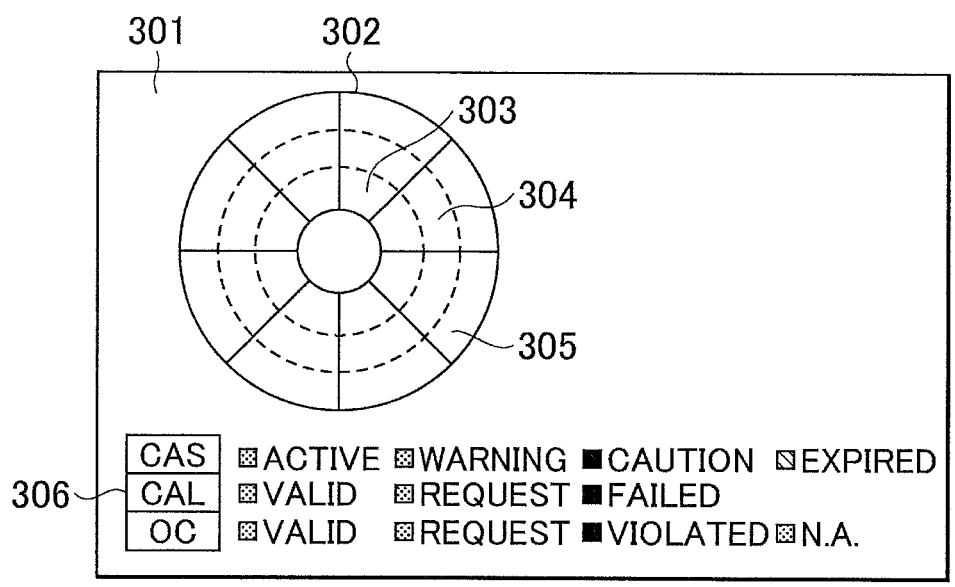
FIG. 3 is a view illustrating an example of a screen for displaying thereon information concerning a plurality of reagents.

FIG. 3 is a block diagram illustrating a screen for checking the states of reagents, calibrator, and quality control in a display system according to the present invention. A reagent disk 302 for reagent information corresponding to the number of positions on an apparatus, a reagent status display position 303 for each reagent, a calibration status display position 304, a QC status display position 305, and color information indicating a status displayed on each status position are displayed on a reagent overview screen 301. The color information displayed at each status position is displayed with colors set in the status display color information 306 for reagent information based on results of the operations performed on the screens shown in FIGS. 4-6 respectively.

Figure 4:
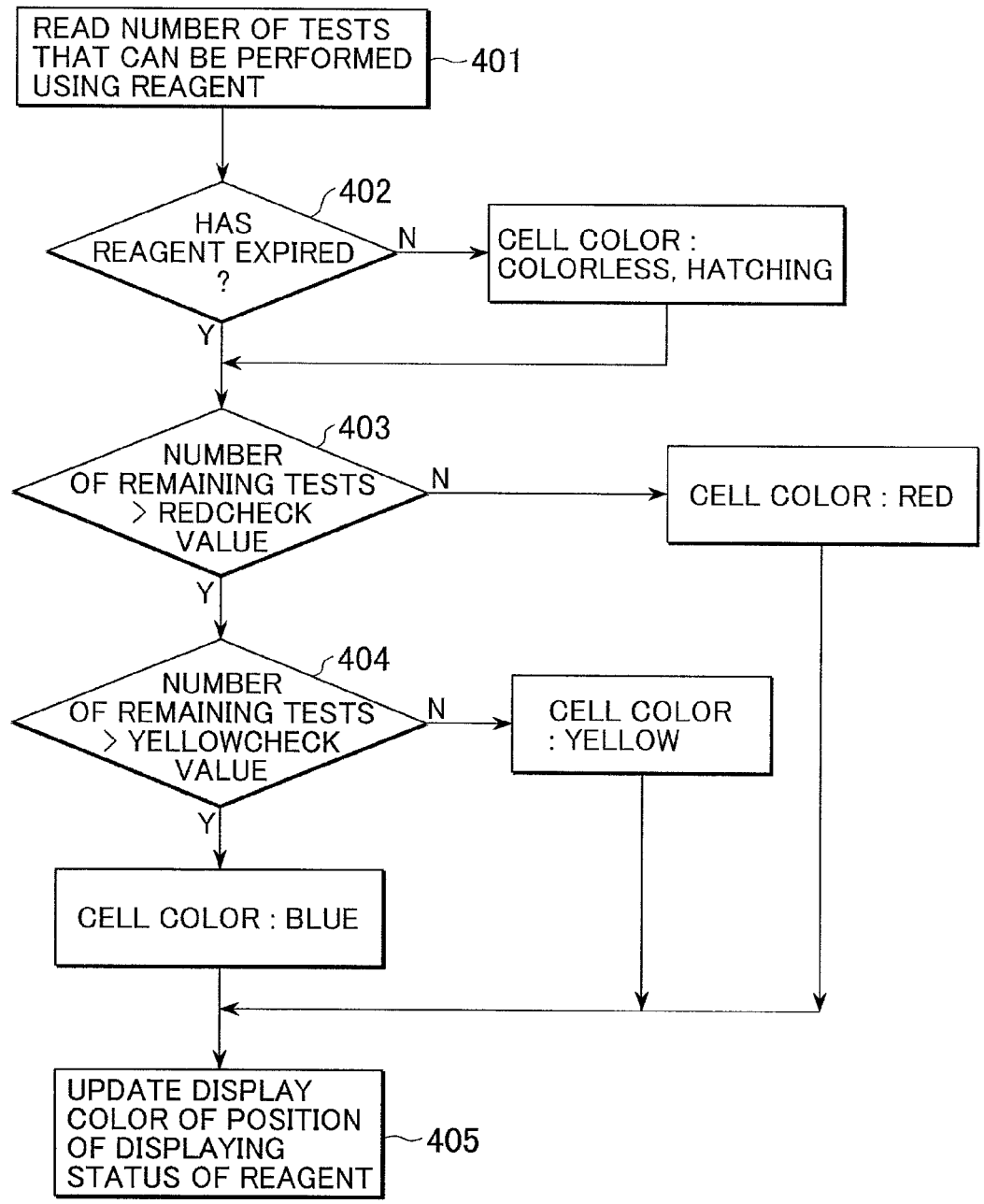
FIG. 4 is a flow chart illustrating a process for determining a status of a reagent and a display color for the status.

FIG. 4 is a flow illustrating a process of determining a status of reagent information and display color corresponding to the status. For each position of a reagent, reagent information is read (401), an expiration date of the reagent is checked (402), a Red Check range is checked (403), and a Yellow Check range is checked (404), and a display color for the reagent status display position 303 is updated based on the results of checking above (405).

Figure 5:
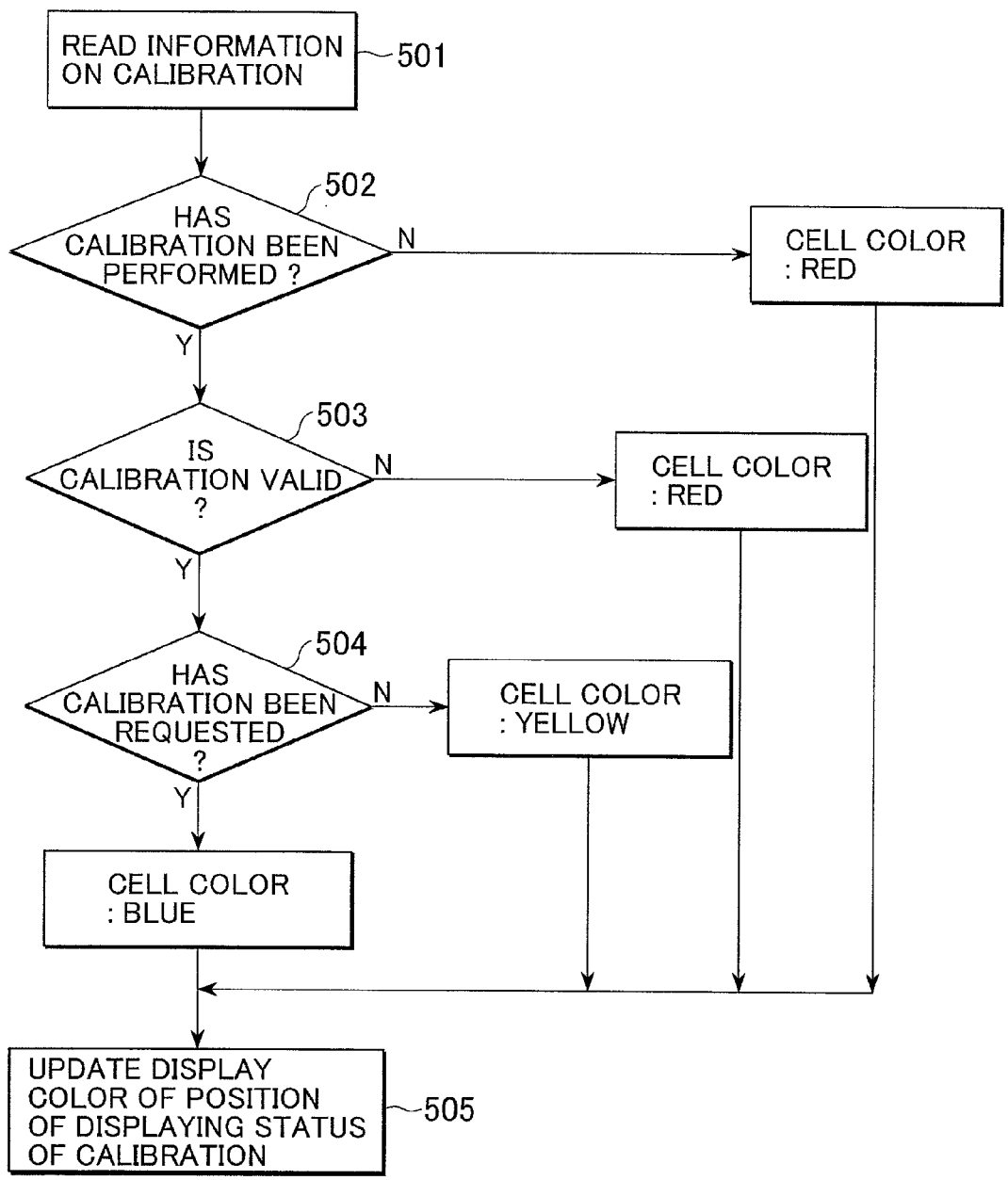
FIG. 5 is a flow chart illustrating a process for determining a status of calibration and a display color corresponding to the state.

FIG. 5 is a flow illustrating a process for determining a status of a calibration and a display color corresponding to the status. For each reagent position, calibration information is read (501), whether calibration is to be performed or not is checked (502), whether the calibration data is valid is checked (503), and whether a request for calibration has been issued is checked (504), and a display color for the calibration status display position 304 is updated (505).

Figure 6:
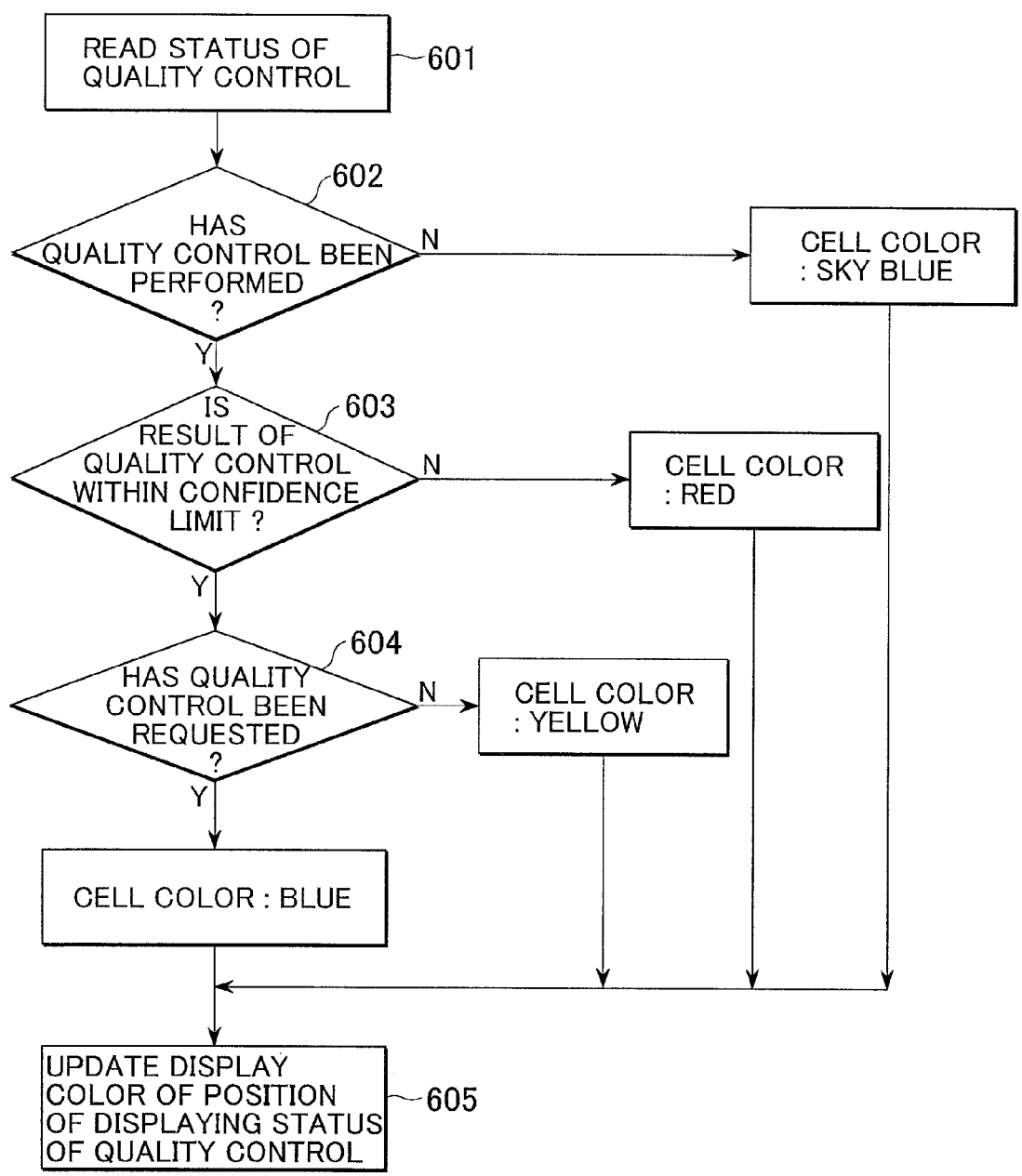
FIG. 6 is a flow chart illustrating a process for determining a status of quality control and a display color corresponding to the status.

FIG. 6 is a flow illustrating a process for determining status of quality control and a display color corresponding to the QC status. For each reagent position, QC information is read (601), whether quality control is to be performed is checked (602), a confidence limit range is checked (603), and whether a request for quality control has been issued is checked (604), and then a display color for the QC status display position 305 is updated (606).

The processes shown in 4-6 are repeated corresponding to the number of reagent positions shown in the reagent disk, and the status of each of the reagents placed in the reagent disk are displayed on the screen. Thus, a plurality of information can be simultaneously displayed and one or more problematic reagents can be easily identified.

What is claimed is:

1. An automatic analyzer comprising:

an analysis section for analyzing a sample;

a reagent mounting disk mounting a plurality of reagents thereon; and a display section having a screen for displaying different types of information on the screen concerning each reagent mounted on the reagent mounting disk, the different types of information for each reagent including a position of the reagent mounted on the mounting disk, a reagent status of each reagent, a calibration status of each reagent and a quality control status of each reagent, whether a calibration is to be performed or not for each reagent, whether a calibration data is valid or not for each reagent, whether a request for a calibration has been issued or not for each reagent, whether a quality control is to be performed or not for each reagent, whether a result of quality control is within a confidence limit range or not for each reagent, and whether a request for quality control has been issued or not for each reagent;

the screen displaying the reagents positions corresponding to physical positions of the reagents mounted on the reagent mounting disk and at the same time displaying information for the reagent status of each reagent, whether the calibration is to be performed or not for each reagent, whether the calibration data is valid or not for each reagent, whether the request for a calibration has been issued or not for each reagent, whether the quality control is to be performed or not for each reagent, whether the result of quality control is within the confidence limit range or not for each reagent, and whether the request for quality control has been issued or not for each reagent; and the screen being configured to display each display position in a display color corresponding to a result of a status check regarding the information on the reagent status of each regent, whether the calibration is to be performed or not for each reagent, whether the calibration data is valid or not for each reagent, whether the request for a calibration has been issued or not for each reagent, whether the quality control is to be performed or not for each reagent, whether the result of quality control is within the confidence limit range or not for each reagent, and whether the request for quality control has been issued or not for each reagent, carried out for the reagent mounted at the physical position corresponding to the reagent position.

* * * * *